(12) United States Patent
Nakamura

(10) Patent No.: US 8,418,533 B2
(45) Date of Patent: Apr. 16, 2013

(54) ANALYZING SYSTEM FOR LIQUID CHROMATOGRAPH AND CONTROL PROGRAM FOR THE SAME SYSTEM

(75) Inventor: Takafumi Nakamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 291 days.

(21) Appl. No.: 13/042,280

(22) Filed: Mar. 7, 2011

(65) Prior Publication Data

US 2011/0219859 A1 Sep. 15, 2011

(30) Foreign Application Priority Data

Mar. 10, 2010 (JP) .................................. 2010-052975

(51) Int. Cl.
*G01N 30/84* (2006.01)
(52) U.S. Cl.
USPC ........................................ 73/61.55; 73/61.59
(58) Field of Classification Search .................. 73/61.55, 73/61.59
See application file for complete search history.

(56) References Cited

U.S. PATENT DOCUMENTS

| | | | | |
|---|---|---|---|---|
| 6,577,392 B1* | 6/2003 | Nielsen et al. | .................. | 506/12 |
| 6,770,876 B2* | 8/2004 | Gu et al. | ....................... | 250/288 |
| 6,823,278 B1* | 11/2004 | Carney et al. | .................... | 702/94 |
| 6,846,455 B1* | 1/2005 | Carney et al. | .................... | 422/64 |
| 6,859,271 B1* | 2/2005 | Carney et al. | ................. | 356/244 |
| 2012/0304745 A1* | 12/2012 | Heden et al. | ................. | 73/61.55 |
| 2013/0014566 A1* | 1/2013 | Marks | .......................... | 73/61.55 |

FOREIGN PATENT DOCUMENTS

| | | |
|---|---|---|
| JP | 10-281948 | 10/1998 |
| JP | 11-201961 | 7/1999 |

* cited by examiner

*Primary Examiner* — J M Saint Surin
(74) *Attorney, Agent, or Firm* — DLA Piper LLP (US)

(57) ABSTRACT

The present invention provides an analyzing system with which a serial analysis inclusive of a pretreatment can be easily performed in a liquid chromatograph, and even unskilled users can perform a desired analysis. The analyzing system according to the present invention includes: an edit screen display section 31 for displaying an edit screen for allowing a user to create a pretreatment program using an external variable; a batch table display section 32 for displaying a batch table used for serially executing a plurality of analyses, the batch table having an external-variable setting field for allowing the user to enter the aforementioned external variable; and a serial analysis execution section 33 for serially executing each of the analyses inclusive of a pretreatment operation of an auto-sampler according to the pretreatment program and the batch table.

2 Claims, 6 Drawing Sheets

| Batch Table | | | | | | |
|---|---|---|---|---|---|---|
| Folder : G:¥LCsolution | | | | | | |
| ANALY-SIS | Vial No. | Tray | Method File | Data File | Injection Volume | ... |
| 1 | 1 | 1 | sample.lcm | data001.lcd | 1 | ... |
| 2 | 2 | 1 | sample.lcm | data002.lcd | 1 | ... |
| 3 | 3 | 1 | sample.lcm | data003.lcd | 1 | ... |

Fig. 1

| Batch Table | | | | | |
|---|---|---|---|---|---|
| Folder : G:¥LCsolution | | | | | |
| ANALY-SIS | Vial No. | Tray | Method File | Data File | Injection Volume | ... |
| 1 | 1 | 1 | sample.lcm | data001.lcd | 1 | ... |
| 2 | 2 | 1 | sample.lcm | data002.lcd | 1 | ... |
| 3 | 3 | 1 | sample.lcm | data003.lcd | 1 | ... |

Fig. 5

| ANALY-SIS | Vial No. | Tray | Method File | Data File | Injection Volume | B1 | B2 | B3 |
|---|---|---|---|---|---|---|---|---|
| 1 | 1 | 1 | sample.lcm | data001.lcd | 1 | 100 | 1 | 5 |
| 2 | 1 | 1 | sample.lcm | data002.lcd | 1 | 100 | 1 | 10 |
| 3 | 1 | 1 | sample.lcm | data003.lcd | 1 | 100 | 1 | 15 |
| 4 | 1 | 1 | sample.lcm | data004.lcd | 1 | 100 | 1 | 20 |
| 5 | 1 | 1 | sample.lcm | data005.lcd | 1 | 100 | 1 | 25 |
| 6 | 1 | 1 | sample.lcm | data006.lcd | 1 | 200 | 1 | 5 |
| 7 | 1 | 1 | sample.lcm | data007.lcd | 1 | 200 | 1 | 10 |
| 8 | 1 | 1 | sample.lcm | data008.lcd | 1 | 200 | 1 | 15 |
| 9 | 1 | 1 | sample.lcm | data009.lcd | 1 | 200 | 1 | 20 |
| 10 | 1 | 1 | sample.lcm | data010.lcd | 1 | 200 | 1 | 25 |

Batch Table
Folder : G:\LCsolution 321
322

Fig. 6

Batch Table
Folder : G:¥LCsolution

| ANALY-SIS | Vial No. | Tray | Method File | Data File | Injection Volume | Vial | Tray | Additive Volume |
|---|---|---|---|---|---|---|---|---|
| 1 | 1 | 1 | sample.lcm | data001.lcd | 1 | 100 | 1 | 5 |
| 2 | 1 | 1 | sample.lcm | data002.lcd | 1 | 100 | 1 | 10 |
| 3 | 1 | 1 | sample.lcm | data003.lcd | 1 | 100 | 1 | 15 |
| 4 | 1 | 1 | sample.lcm | data004.lcd | 1 | 100 | 1 | 20 |
| 5 | 1 | 1 | sample.lcm | data005.lcd | 1 | 100 | 1 | 25 |
| 6 | 1 | 1 | sample.lcm | data006.lcd | 1 | 200 | 1 | 5 |
| 7 | 1 | 1 | sample.lcm | data007.lcd | 1 | 200 | 1 | 10 |
| 8 | 1 | 1 | sample.lcm | data008.lcd | 1 | 200 | 1 | 15 |
| 9 | 1 | 1 | sample.lcm | data009.lcd | 1 | 200 | 1 | 20 |
| 10 | 1 | 1 | sample.lcm | data010.lcd | 1 | 200 | 1 | 25 |

321
322

ANALYZING SYSTEM FOR LIQUID CHROMATOGRAPH AND CONTROL PROGRAM FOR THE SAME SYSTEM

The present invention relates to an analyzing system including an auto-sampler (i.e. automatic sampling device for liquid samples) for injecting a liquid sample into a liquid chromatograph, and also to a program for controlling such an analyzing system.

BACKGROUND OF THE INVENTION

Liquid chromatograph systems often use an auto-sampler to analyze a number of liquid samples. In this system, liquid samples are prepared beforehand in a plurality of vials of the auto-sampler. These samples can be individually and serially selected in a predetermine order and injected into a column of the liquid chromatograph. After setting a number of samples in the rack of the auto-sampler, the user (analysis operator) sets necessary information, such as the analyzing order of the samples and the analysis conditions, on a personal computer for controlling the auto-sampler. For example, a batch table (schedule table) as shown in FIG. 1 is displayed on the screen of the personal computer, on which the user can set necessary information. Subsequently, the user enters a command for initiating the analysis, whereupon the system performs a serial analysis, in which each sample are selected in the order specified in the batch table and an analysis is performed on the selected sample under the specified conditions (JP-A H11-201961).

In recent years, liquid chromatographs have been used for analyzing an extremely wide range of samples with increasingly complex structures. To perform an accurate analysis for each of a variety of samples, it is necessary, in some cases, to perform various pretreatments on the selected liquid sample before injecting it into the column. For example, the pretreatment includes condensing or diluting a sample component, removing unnecessary or interfering components, or adding a reagent. Some auto-samplers originally have such pretreatment functions. However, to use these functions, a pretreatment program must be created beforehand, as shown in FIG. 2, to control the operation of the auto-sampler (JP-A H10-281948).

In conventional analyzing systems, the process of controlling the auto-sampler before or during the analysis includes selecting a correct vial in which a desired sample is contained, regulating the volume of the sample injected into the column, and so on. However, it is impossible to control the entire pretreatment operation. Accordingly, for example, when a serial analysis is performed on a plurality of samples each requiring a different mode of pretreatment, such as a different amount of reagent or different kind of reagent, it is necessary to describe all the required modes of pretreatments in the pretreatment program.

The pretreatment program for controlling the operation of the auto-sampler is extremely complex and long. Even an expert user needs a considerable amount of time to rewrite a pretreatment program. For unskilled users, rewriting a pretreatment program is extremely difficult in the first place, so it is difficult for them to perform the analysis as desired.

The problem to be solved by the present invention is to provide an analyzing system with which a serial analysis inclusive of a pretreatment can be easily performed in a liquid chromatograph, and even unskilled users can perform a desired analysis. The present invention is also aimed at providing a control program for such an analyzing system.

SUMMARY OF THE INVENTION

Thus, the present invention aimed at solving the aforementioned problem provides an analyzing system for a liquid chromatograph having an auto-sampler capable of performing a pretreatment operation according to a pretreatment program, including:

an edit screen display means for displaying an edit screen for allowing a user to create the pretreatment program using an external variable;

a batch table display means for displaying a batch table used for serially executing a plurality of analyses, the batch table having an external-variable setting field for allowing the user to enter the aforementioned external variable; and a serial analysis execution means for serially executing each of the analyses inclusive of the pretreatment operation of the auto-sampler according to the pretreatment program and the batch table.

The present invention also provides a control program for an analyzing system for a liquid chromatograph having an auto-sampler capable of performing a pretreatment operation according to a pretreatment program, wherein the control program makes a computer function as a system having:

an edit screen display section for displaying an edit screen for allowing a user to create the pretreatment program using an external variable;

a batch table display section for displaying a batch table used for serially executing a plurality of analyses, the batch table having an external-variable setting field for allowing the user to enter the aforementioned external variable; and a serial analysis execution section for serially executing each of the analyses inclusive of the pretreatment operation of the auto-sampler according to the pretreatment program and the batch table.

The "external variable" in the present invention means any variable corresponding to a numerical value, command or other kinds of information that are externally given (through the external-variable setting field in the batch table) to the pretreatment program to be actually used inside the same program.

The gist of the present invention is that one or more numerical values or commands used inside the pretreatment program are provided as external variables that can be manually entered in a batch table used for the scheduling of the serial analysis. Users need only to change the values of the external-variable setting fields in the batch table to control the operation of the auto-sampler. There is no need to directly rewrite the pretreatment program for each analysis. Therefore, an analysis inclusive of a pretreatment can be easily executed. After a pretreatment program using the external variables is created by an expert user, even an unskilled user can easily control the operation of the auto-sampler to conduct a desired analysis.

BRIEF DESCRIPTION OF THE DRAWINGS

FIG. 1 shows an example of a batch table displayed on a screen when a serial analysis is executed.

FIG. 5 shows an example of the batch table in the present embodiment.

FIG. 6 shows a modified example of the batch table according to the present embodiment.

DETAILED DESCRIPTION OF A PREFERRED EMBODIMENT

An analyzing system for a liquid chromatograph, which is one embodiment of the present invention, is hereinafter described with reference to the attached drawings.

Figure 3A:
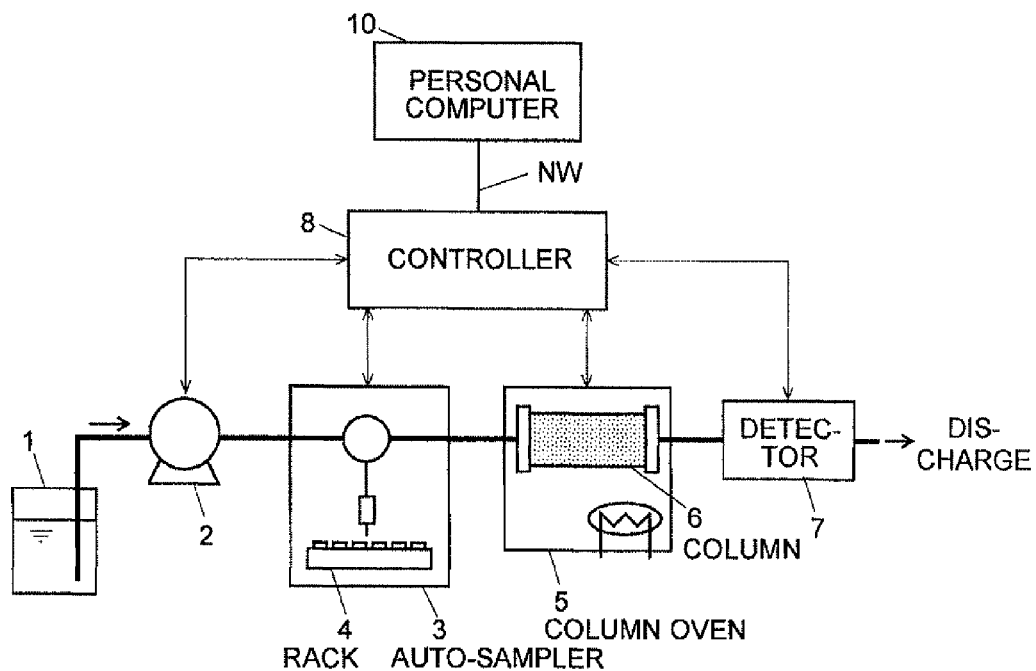
FIG. 3A is a configuration diagram of an analyzing system for a liquid chromatograph according to one embodiment of the present invention.

As shown in FIG. 3A, the analyzing system for a liquid chromatograph according to the present embodiment includes a tank 1 for storing an eluent (mobile phase), a liquid supply pump 2, an auto-sampler 3, a column 6 contained in a column oven 5, a detector 7, a controller 8 for controlling the previously listed devices, and a personal computer (PC) 10 for conducting analytical tasks through the controller 8 and for analyzing and processing the data obtained with the detector 7.

Figure 3B:
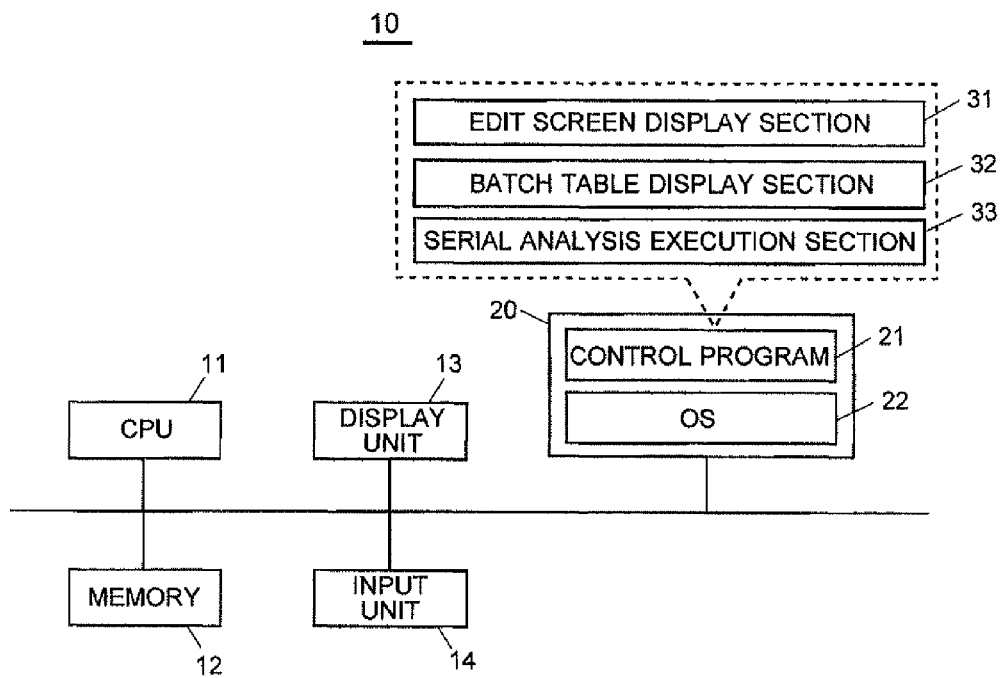
FIG. 3B is a schematic configuration diagram of the personal computer shown in FIG. 3A.

FIG. 3B is a schematic configuration diagram of the PC 10. This PC 10 includes a central processing unit (CPU) 11, a memory 12, a monitor (display unit) 13 consisting of a liquid crystal display (LCD) and other components, an input unit 14 consisting of a keyboard, mouse and other components, and a storage unit 20 consisting of a large-capacity storage device, such as a hard-disk drive. These components are all connected to each other via communication lines. The storage unit 20 has a control program 21, an operating system (OS) 22 and other software components installed therein.

The control program 21 includes an edit screen display section 31, a batch table display section 32 and a serial analysis execution section 33, which implement the characteristic functions of the present invention. These sections are the software components realized by running the control program 21 on the CPU 11.

Figure 2:
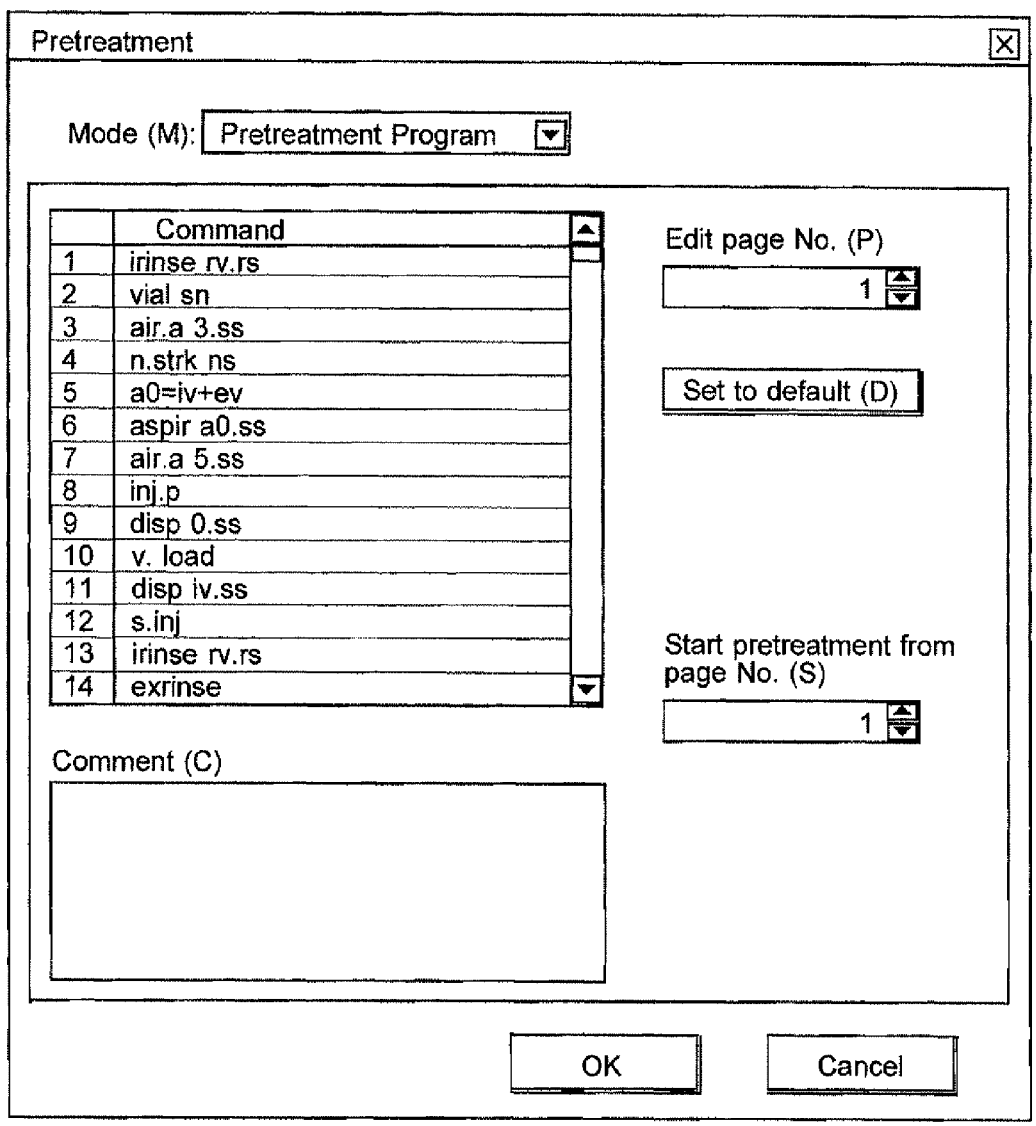
FIG. 2 shows an example of an edit screen displayed on a screen when a pretreatment program is created.
Figure 4:
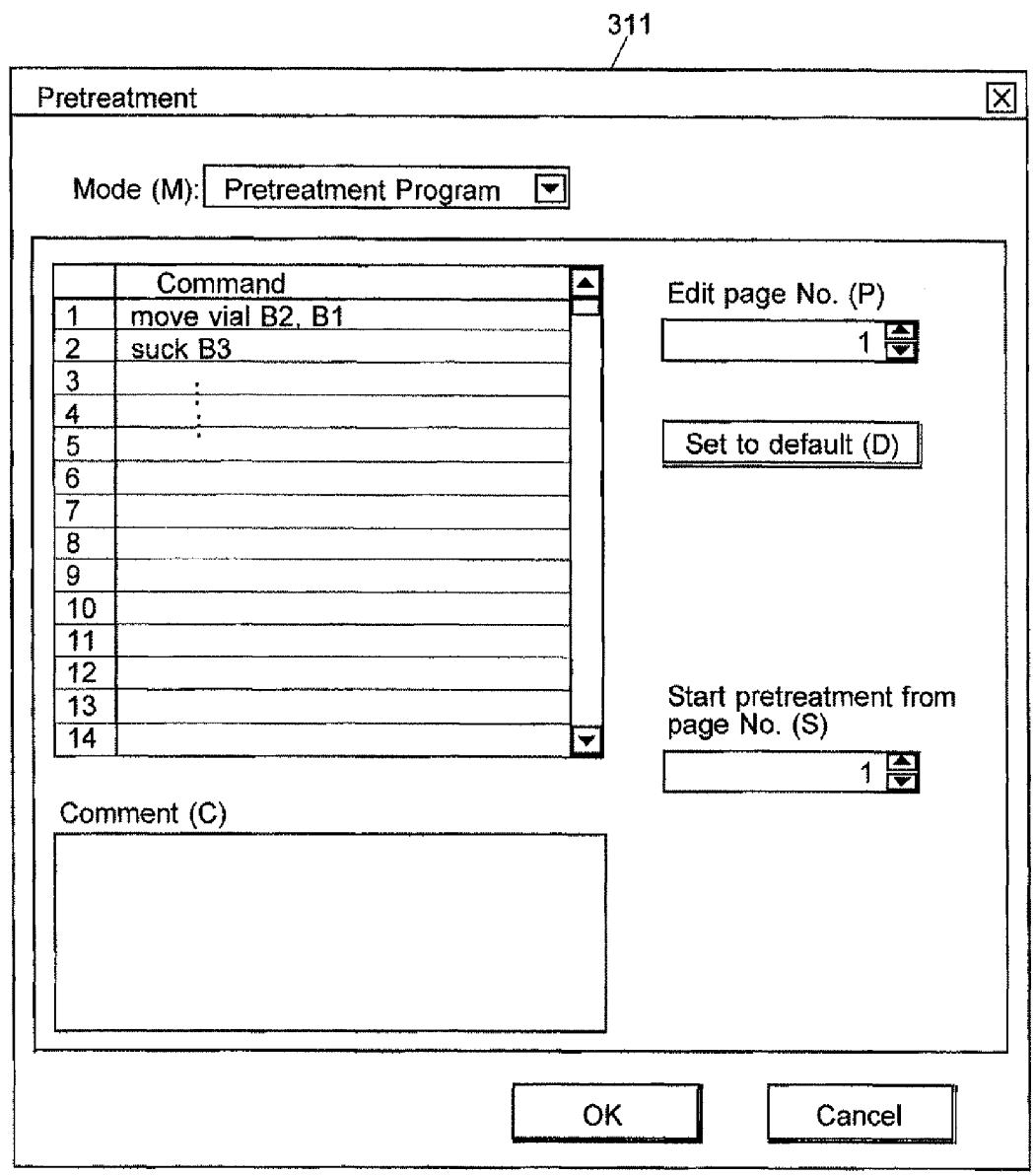
FIG. 4 shows an example of the pretreatment program in the present embodiment.

The edit screen display section 31 displays a pretreatment program edit screen 311, as shown in FIG. 4, on the screen of the monitor 13. The basic design of this edit screen 311 is the same as that of the edit screen shown in FIG. 2. The most important difference from the conventional example exists in the use of predetermined external variables representing numerical values or commands in a pretreatment program created on the edit screen 311 by a user. In the case of FIG. 4, "B1", "B2" and "B3" are external variables. It should be noted that FIG. 4 shows only a portion of the pretreatment program.

The external variables must have unique names different from those of the other commands or parameters used in the pretreatment program. It is possible to specify, on the system side, the choices of external-variable names available for users and/or the maximum number of the available names.

On the other hand, the batch table display section 32 displays a batch table 321, as shown in FIG. 5, on the screen of the monitor 13. This batch table 321 differs from the conventional example shown in FIG. 1 in that external-variable setting fields 322 are provided. The batch table 321 has the following fields (from left to right): the analysis order, the number of the vial containing a sample to be analyzed, the number of the tray on which the vial is placed, the name of the method file in which the analysis conditions are described (e.g. the temperature of the column oven 5, the flow rate of the sample in the column 6, and so on), the name of the data file to save the analysis data, the volume of the sample to be injected into the column, and the external-variable setting fields 322.

The external-variable setting fields 322 are for entering numerical values or other information based on the objectives of each external variable used in the pretreatment program. For example, when the variables B1, B2 and B3 respectively correspond to the vial number, tray number and additive amount, the schedule prepared in the batch table 321 of FIG. 5 can be interpreted as follows: For the sample contained in vial No. 1 on tray No. 1, a serial analysis is executed using the additive reagent contained in vial No. 100 while changing the amount of reagent from 5 $\mu$L to 25 $\mu$L. Subsequently, the serial analysis is similarly executed for the sample contained in vial No. 2 on tray No. 1, using the additive reagent contained in vial No. 200 while changing the amount of reagent from 5 $\mu$L to 25 $\mu$L.

In the case of the pretreatment program shown in FIG. 4, the variables B1, B2 and B3 respectively represent the vial number, tray number and suction volume. If the pretreatment program is written as follows:

move vial B2, B3
dilute B1 then the variables B1, B2 and B3 respectively represent the dilution amount, vial number, and tray number. These examples illustrate that the objectives of external variables in a pretreatment program can change depending on their usage in the pretreatment program. Users can freely determine the usage of each external variable.

The serial analysis execution section 33 gives the controller 8 a series of instructions relating to the analysis conditions or the like in the order as specified in the batch table 321. An analysis operation in the analyzing system of the present embodiment is hereinafter described.

Under the control of the controller 8 receiving instructions from the PC 10, the liquid supply pump 2 suctions the eluent from the tank 1 at an approximately constant flow rate and supplies it through the auto-sampler 3 into the column 6. In the auto-sampler 3, a sample rack 4 carrying a number of vials is previously set. According to a pretreatment program created on the edit screen 311 and the batch table 321, the auto-sampler 3 carries out a pretreatment operation and injects the sample held the pretreated vial into the eluent, which carries the injected sample into the column 6. The length of time required for each component in the sample to pass through the column 6 (retention time) varies depending on the component. As a result, the components in the sample are temporally separated while passing through the column 6. The detector 7 sequentially detects each of these components separated by and eluted from the column 6. The detection data are sent through the controller 8 to the PC 10. These operations are sequentially performed in the order specified in the batch table 321.

The analyzing system for a liquid chromatograph according to the present invention has been described thus far by means of an embodiment. It should be noted that the previous embodiment is a mere example of the present invention, and any change, modification or addition can be appropriately made within the gist of the present invention.

For example, in the previous embodiment, the objectives of external variables change depending on their usage in the pretreatment program. As opposed to that, it is possible to fix, on the system side, the name of the external variable for each usage. In this case, words or phrases showing the meanings of the variables can be displayed in place of the variable names in the top row of the external-variable setting fields, as shown in FIG. 6.

EXPLANATION OF NUMERALS

1 ... Eluent Tank
2 ... Liquid Supply Pump
3 ... Auto-Sampler
4 ... Sample Rack
5 ... Column Oven
6 ... Column
7 ... Detector
8 ... Controller
10 ... Personal Computer (PC)
11 ... Central Processing Unit (CPU)
12 ... Memory
13 ... Monitor
14 ... Input Unit
20 ... Storage Unit
21 ... Control Program
22 ... Operating System (OS)
31 ... Edit Screen Display Section
311 ... Edit Screen
32 ... Batch Table Display Section
321 ... Batch Table
322 ... External-Variable Setting Fields
33 ... Serial Analysis Execution Section

What is claimed is:

1. An analyzing system for a liquid chromatograph having an auto-sampler configured to perform a pretreatment operation according to a pretreatment program, comprising:

an edit screen display means for displaying an edit screen for allowing a user to create the pretreatment program using an external variable;

a batch table display means for displaying a batch table used for serially executing a plurality of analyses, the batch table having an external-variable setting field for allowing the user to enter the aforementioned external variable; and a serial analysis execution means for serially executing each of the analyses inclusive of the pretreatment operation of the auto-sampler according to the pretreatment program and the batch table.

2. An analyzing system for a liquid chromatograph having an auto-sampler configured to perform a pretreatment operation according to a pretreatment program, wherein the control program makes a computer function as a system having:

an edit screen display section for displaying an edit screen for allowing a user to create the pretreatment program using an external variable;

a batch table display section for displaying a batch table used for serially executing a plurality of analyses, the batch table having an external-variable setting field for allowing the user to enter the aforementioned external variable; and a serial analysis execution section for serially executing each of the analyses inclusive of the pretreatment operation of the auto-sampler according to the pretreatment program and the batch table.

* * * * *